(12) United States Patent
Vic et al.

(10) Patent No.: US 9,433,804 B2
(45) Date of Patent: Sep. 6, 2016

(54) MAKE-UP COMPOSITION PRODUCING A CHANGE IN COLOUR ON APPLICATION

(75) Inventors: Sabine Vic, Semoy (FR); Fabienne Brossard, Orleans (FR); Brigitte Noe, Orleans (FR); Eric Perrier, Les Cotes d'Arey (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 289 days.

(21) Appl. No.: 13/471,837

(22) Filed: May 15, 2012

(65) Prior Publication Data

US 2012/0315232 A1 Dec. 13, 2012

(30) Foreign Application Priority Data

May 26, 2011 (FR) .................................... 11 54592

(51) Int. Cl.
*A61Q 1/06* (2006.01)
*A61K 8/02* (2006.01)
*A61K 8/19* (2006.01)
*A61K 8/81* (2006.01)
*A61K 8/88* (2006.01)

(52) U.S. Cl.
CPC . *A61Q 1/06* (2013.01); *A61K 8/02* (2013.01); *A61K 8/0229* (2013.01); *A61K 8/19* (2013.01); *A61K 8/8117* (2013.01); *A61K 8/88* (2013.01); *A61K 2800/262* (2013.01); *A61K 2800/31* (2013.01); *A61K 2800/43* (2013.01); *A61K 2800/88* (2013.01)

(58) Field of Classification Search
CPC .. A61K 8/88; A61K 2800/262; A61K 8/442; A61K 2800/31; A61K 8/02; A61K 8/8111; A61K 2800/43; A61K 2800/438; A61K 2800/594; A61K 2800/88; A61K 8/044; A61K 8/25; A61K 8/37; A61K 8/891
See application file for complete search history.

(56) References Cited

U.S. PATENT DOCUMENTS

| 5,382,433 A | 1/1995 | Pahlck et al. |
| 5,437,859 A * | 8/1995 | Ser et al. ................ 424/59 |
| 6,469,131 B2 * | 10/2002 | Lawson et al. ............ 528/335 |
| 7,461,987 B2 * | 12/2008 | Liechty et al. ............. 401/47 |
| 2009/0280076 A1 | 11/2009 | Yoshida et al. |
| 2009/0280077 A1 * | 11/2009 | Yoshida et al. ............ 424/59 |
| 2010/0221205 A1 | 9/2010 | Blin et al. |
| 2011/0243862 A1 | 10/2011 | Vic et al. |

FOREIGN PATENT DOCUMENTS

| CA | 2 278 685 | 8/1998 |
| DE | 197 07 309 | 8/1998 |
| EP | 1 745 770 | 1/2007 |
| EP | 2 156 821 | 2/2010 |
| EP | 2 198 826 | 6/2010 |
| FR | 2 908 643 | 5/2008 |
| FR | 2 908 656 | 5/2008 |
| FR | 2 925 300 | 6/2009 |
| FR | 2 958 159 | 10/2011 |
| WO | WO01/97758 | 12/2001 |
| WO | WO2009/080623 | 7/2009 |

OTHER PUBLICATIONS

"Haimalate PAM" data sheet, accessed online Sep. 4, 2014.*

* cited by examiner

*Primary Examiner* — Audrea Buckley
(74) *Attorney, Agent, or Firm* — Hamre, Schumann, Mueller & Larson, P.C.

(57) ABSTRACT

The invention relates to a cosmetic composition for making up the skin, lips or superficial body growths, comprising
a cosmetic base,
at least one colored inorganic pigment [A] in an amount sufficient to define a first color of said composition in its body, and
at least one pigment [B] chosen from organic dye lakes, the color of which is different from that of the pigment [A], in an amount sufficient to define a second color, radically different from said first color, which is revealed after the application of said composition on the lips, skin or superficial body growths.

9 Claims, No Drawings

MAKE-UP COMPOSITION PRODUCING A CHANGE IN COLOUR ON APPLICATION

The invention relates to a cosmetic composition intended for making up the skin, lips or superficial body growths, to a range of products each comprising such a composition and to a make-up method employing this composition.

STATE OF THE ART

Make-up compositions for the skin or lips are formulated so that the film applied has the characteristics expected both from the visual viewpoint (colour, hue) and from the mechanical viewpoint (persistence of the film).

Mention may be made, among the usual criteria for selecting colouring agents used for the formulation of a make-up composition, of the "colouring power" of a colouring agent, which represents the ability of the colouring agent to faithfully communicate its colour to the body of the composition, and the "covering power" of a colouring agent, that is to say its ability, at a given concentration, to cover a substrate on which the composition is applied in a homogeneous fashion in the form of a film to which it communicates its colour.

In the case of compositions for making up the skin or lips, it is preferable to look for colouring agents having colouring and covering properties which make it possible to obtain a make-up having a colour rendering, once the composition has been applied to the skin or lips, independent of the native colour of the non-made-up skin or lips. This uniformity in colour between the body of the composition and the film applied is desired by formulators in order for the user to be able to correlate the colour of the composition which she notices on purchase with the colour of the film which she will apply to the lips.

In the compositions provided in the form of a stick, for example, such as lipstick sticks, the strong opacifying power of titanium dioxide is commonly used to render the hue and the intensity in colour of the film applied uniform with those of the body of the stick.

Mood lipsticks, which change colour according to the mood of the person using them, have been proposed. As it is possible for the temperature or the pH of the skin to vary as a function of a large number of physiological factors, such as hormonal fluctuations, the stress state, the level of physical a colour which is substantially different according to the state of the person at the time of the application of a composition comprising a dye or a pigment sensitive to one of these factors.

Such products comprise dyes or pigments which are sensitive to modifications to the surroundings on which they are applied.

One category of compounds having a colour which can vary according to the physiological state of the skin are weak acids, the conjugated base of which has a colour radically different from that of the acid form. They are commonly used as pH indicators. For example, eosin changes colour according to the pH of the contact medium.

Another category relates to "thermochromic" compounds, which change in colour according to the temperature of the contact medium. There also exist photochromic compounds, which change colour once exposed to UV radiation.

Finally, some colouring agents are sensitive to oxidation and change colour on contact with oxygen.

In view of the number of physiological factors capable of influencing the pH or the temperature of the skin or lips, it is particularly difficult to obtain a film producing a colour which is perfectly reproducible for one application to the other starting from compositions comprising such dyes and pigments.

Moreover, these formulations are also capable of changing colour over time if a change in temperature occurs during the storage of the product, which is not desirable.

One alternative to mood lipsticks is based on the use of a covering base (base coat) applied prior to a colouring surface layer (top coat), said covering base having properties which modify the properties of the surface layer (top coat) so as to bring about the desired change in colour. However, this requires the use of two separate formulations, which renders the make-up action more complex.

The disadvantages of the products of the prior art thus make it particularly necessary to make available, to users, make-up compositions which deposit on the skin, lips or superficial body growths a film having a colour which is different from the colour of the composition as provided before the use thereof, this change in colour being independent of the pH or temperature state of the skin, lips or superficial body growths on which it is applied.

Provision has been made, in the document FR 2 908 643, to incorporate, in a make-up composition, two pigments which reflect a different intensity and a different wavelength as a function of the incident light. The composition comprises pigments having an optical effect, such as interferential pigments.

In the document FR 2 908 656, the change in colour of the product during application is obtained by coextruding two compositions of different colours, so that a lipstick stick, for example, is composed of two halves having different colours. In this document, the change in colour noted between the appearance of the make-up product and the colour of its deposited layer on the skin is obtained by using two different compositions which have been coextruded.

AIMS OF THE INVENTION

The present invention is thus targeted at providing a composition intended in particular for caring for or making up the skin, lips or superficial body growths.

Another aim of the present invention is to provide a range of make-up products exhibiting, in their body, substantially identical colours, so that it is impossible, for an average user, to distinguish two different products by their colours, said products providing different colours once applied to the skin, lips or superficial body growths.

Colour in a body is understood to mean the colour of the composition as it is perceived when the composition is packaged and ready for use. This can be colour of a lipstick cast as a stick or poured into a jar, the colour of a lip gloss or a face powder which has been packaged in a small bottle or poured into a jar, or the colour of a nail varnish packaged in a transparent glass bottle or in any other suitable transparent packaging which allows the colour of the body of the product to be perceived. The thickness of the composition according to the invention before it is applied on the skin is generally between 5 and 20 mm.

Another aim of the present invention is to provide a method for the preparation of such compositions while optimizing the desired colours or variations and while limiting the risks of incompatibility and/or of instability which may detrimentally affect the hue of the colour obtained.

Another aim of the present invention is to provide a make-up method which is simple for the user.

A further aim of the invention is to solve the technical problems in a reliable and reproducible way which can be used on an industrial scale, in particular in cosmetics.

SUMMARY OF THE INVENTION

The Applicant has discovered, surprisingly, that it is possible to obtain such a result by combining organic dye lakes with an inorganic pigment, such as an iron oxide.

The colour of the composition according to the invention as visually perceived when a user looks at it before using it is different from the colour of the composition perceived visually once the latter has been applied as a thin layer on a support, such as the skin, lips or nails.

The inventors of the present invention have obtained compositions which differ from the compositions of the prior art in particular in that the colour emitted by the composition applied in the form of a film on the lips is completely different from the colour of the composition in its body. This difference in the perception of the colour results in particular from the difference in thickness between the composition observed in its packaging (generally of between 5 and 20 mm) and the thickness of the deposited layer of the composition applied on the skin or lips (less than 1 mm, generally between a few tens of and a few hundred microns). The change in colour observed with the mixture of specific pigments according to the invention does not require the use of compounds having a colour sensitive to the conditions of the environment or substrate, in particular pH, temperature, presence of oxygen or incident light.

The invention relates in particular to compositions having a colour which changes when they are applied to the skin, lips or nails. The aim is more particularly to obtain compositions for which the contrasting colour before and after application is as great as possible. The compositions of the invention thus differ fundamentally from conventional make-up compositions for which an identity in hue between the composition in its packaging and the deposited layer of this composition on the skin, lips or superficial body growths is generally sought, so as to make it easier for the user to choose the colour which she desires.

This result is obtained in particular for compositions comprising the mixture of at least one coloured inorganic pigment and at least one lake different in colour from that of the inorganic pigment.

The invention provides for the combining of an inorganic pigment and of an organic dye lake in a transparent base, the lake being in excess with respect to the inorganic pigment. This specific combination makes it possible to give the composition a first colour in its body which corresponds to the colour of the inorganic pigment. Once spread over the skin, the colour of the lakes, which was masked by the colour of the pigment in the body of the composition, is revealed in the deposited layer of the composition, which is generally very thin.

DETAILED DESCRIPTION OF THE INVENTION

Thus, the present invention is targeted at a cosmetic composition for making up the skin, lips or superficial body growths, composed of:
a cosmetic base,
at least one coloured inorganic pigment [A] in an amount sufficient to define a first colour of said composition in its body, and
at least one pigment [B] chosen from organic dye lakes, the colour of which is different from that of the pigment [A], in an amount sufficient to define a second colour, radically different from said first colour, which is revealed after the application of said composition on the lips, skin or superficial body growths.

According to one embodiment, the present invention is targeted at a cosmetic composition for making up the skin, lips or superficial body growths, composed of:
a cosmetic base,
at least one coloured inorganic pigment [A], and
at least one pigment [B] chosen from organic dye lakes, the colour of which is different from that of the pigment [A],
the pigments [A] and [B] being in an amount sufficient for the colour of the composition having a thickness of between 5 and 20 mm to be different from the colour of a deposited layer of the composition having a thickness of less than 1 mm.

Two colours can be regarded as different within the meaning of the present invention, when the $\Delta E^*$ value as defined below differs by at least 10 units, preferably by at least 20 units and preferably by at least 30 units.

Base is understood to mean, within the meaning of the invention, all the ingredients of the composition with the exception of the pigments [A] and [B].

The change in colour can be objectivized by any means which make it possible to demonstrate the differences in colour (or also in hue) between the composition in its body and a film of the composition.

The difference in hue can be observed visually, optionally using a colour chart which makes it possible to characterize the colour of the composition and the colour applied to the skin, lips or superficial body growths.

The difference in hue can also be measured using a CIE Lab colorimetric system which makes it possible to characterize a colour using two hue components a* (red/green axis) and b* (yellow/blue axis), and a lightness component L*.

The $\Delta E^*$ colorimetric difference between two colour samples is given by the formula:

$$\Delta E^* = \sqrt{(L_1-L_2)^2+(a_1-a_2)^2+(b_1-b_2)^2}$$

in which $L_1$, $a_1$ and $b_1$ are the coordinates in the CIE Lab colorimetric space of the first colour and $L_2$, $a_2$ and $b_2$ are those of the second colour.

It is commonly considered that an untrained observer cannot distinguish the difference between two colours for which the $\Delta E^*$ is less than a value of 5 under standard measurement conditions (illuminant $D_{65}$ and observer at 10°).

Two colours can be regarded as different within the meaning of the present invention when the $\Delta E^*$ value, calculated according to the above formula and under standard measurement conditions, is at least 10 units, preferably at least 20 units and preferably at least 30 units.

Within the meaning of the present invention, coloured inorganic pigment [A] is understood to mean an inorganic pigment which is not white: thus, titanium dioxide is excluded from this definition. Given that some cosmetic ingredients, such as titanium dioxide or talc, are opacifiers, it will be preferable to limit the incorporation thereof in the compositions according to the invention, so as to retain the intensity of the change in colour. Generally, it is preferable for the composition to comprise less than 2% by weight of opacifying fillers, in particular less than 1% by weight, and for example less than 1% by weight of titanium dioxide.

According to one embodiment, the composition comprises less than 2% by weight of opacifying filler(s). Mention may be made, among the fillers which have an opacifying nature, of talc, starch, kaolin, zinc and titanium oxides, calcium carbonate, silica, metal soaps derived from organic carboxylic adds, synthetic polymer powders and their mixtures.

Transparent fillers, such as titanium oxide-coated micas, can be incorporated in the cosmetic base of the composition of the invention. Titanium oxide-coated micas within the meaning of the invention are not pigments as they do not contribute any colour to the composition.

The colour of the pigment [A] and the colour of the pigment [B] do not necessarily vary when they are exposed to a change in temperature, to a change in pH or to UV radiation. The pigments used in the composition of the invention are preferably non-thermochromic, non-interferential and non-photochromic, in contrast to the pigments used in the compositions of the prior art, which change in colour on application.

According to one embodiment, it will be preferable for the cosmetic base of the composition to be translucent or substantially transparent in its body. In order to evaluate the transparency of the base, a cosmetic composition according to the present invention which is devoid of pigments can be prepared in the form under which the make-up product is intended to be used, for example in the form of a stick, or poured into a jar. The base for which the transparency is evaluated will preferably have a thickness of 0.5 to 2 cm approximately and will be observed in daylight using the naked eye. The term "translucent" means "which allows light to pass without making it possible to distinguish objects". The term "transparent" means "which allows light to pass and which makes it possible to distinguish objects".

The coloured inorganic pigment [A] can be chosen from carbon black (INCI name CI-77266), iron oxides, manganese violet, ultramarine blue, chromium oxides, in particular chromium oxide hydrate, ferric blue and their mixtures.

The pigments [A] and [B] are preferably monochromic in the sense that they do not reflect an intensity and a wavelength which differ as a function of the incident light. The pigments [A] and [B] are preferably non-interferential pigments.

Mention may be made, among iron oxides, of black iron oxides (of INCI name CI 77499) composed essentially of ferric oxide, yellow iron oxides, red iron oxides and their mixtures.

Advantageously, the pigment [A] is chosen from black iron oxides, carbon black and their mixtures.

The pigment [B] is chosen from organic dye lakes. Organic dyes of natural or synthetic origin are transparent in the liquids which dissolve them. For the colour of these dyes to be detectable at low concentration, they are rendered insoluble in the form of "lakes" by fixing them to an insoluble support.

The organic dye lakes are, for example, lakes of a dye chosen from D&C Black No. 2, FD&C Blue No. 1, FD&C Green No. 3, D&C Green No. 5, D&C Orange No. 4, D&C Orange No. 5, D&C Orange No. 10, D&C No. Red 3, D&C Red No. 6, D&C Red No. 7, D&C Red No. 9, D&C Red No. 13, D&C Red No. 19, D&C Red No. 21, D&C Red No. 22, D&C Red No. 27, D&C Red No. 28, D&C Red No. 30, D&C Red No. 33, D&C Red No. 36, D&C Red No. 40, FD&C Yellow No. 5, FD&C Yellow No. 6, D&C Yellow No. 10 and cochineal carmine.

The composition can also comprise, in addition to the pigments [A] and [B], pearlescent agents which can, for example, be chosen from:
 white pearlescent pigments, such as mica covered with titanium oxide, bismuth oxychloride; and
 coloured pearlescent pigments, such as titanium oxide-coated mica covered with iron oxide, titanium oxide-coated mica covered with ferric blue or with chromium oxide, titanium-oxide coated mica covered with an organic pigment, and pigments based on bismuth oxychloride.

The composition of the invention advantageously comprises:
 at least one coloured inorganic pigment [A] chosen from black iron oxides, carbon black and their mixtures, in an amount sufficient to confer a black colour on the composition in its body, and
 at least one pigment [B] chosen from red, green, yellow and blue pigments, in an amount sufficient to define a colour of the composition film deposited on the skin, lips or superficial body growths which is other than black.

The pigment [B] is preferably chosen from the lakes of a red dye, the lakes of a blue dye, the lakes of a yellow dye, the lakes of a green dye, and their mixtures.

According to a first alternative form, the composition is characterized in that it comprises a lake of a red dye, in an amount sufficient to produce a red film on the skin, lips or nails.

According to a second alternative form, the composition is characterized in that it comprises a lake of a green dye or a mixture of lakes of a blue dye and of a yellow dye, in an amount sufficient to produce a green film on the skin, lips or nails.

According to a third alternative form, the composition is characterized in that it comprises a lake of a blue dye, in an amount sufficient to produce a blue film on the skin, lips or nails.

According to a fourth alternative form, the composition is characterized in that it comprises a lake of a red dye, a lake of a blue dye and a lake of a yellow dye, in an amount sufficient to produce a film coloured raspberry pink on the skin, lips or nails.

According to a fifth alternative form, the composition is characterized in that it comprises a lake of a red dye, a lake of a blue dye and a lake of a yellow dye, in an amount sufficient to produce a film coloured chocolate brown on the skin, lips or nails.

According to a sixth alternative form, the composition is characterized in that it comprises a lake of a red dye, a lake of a blue dye and a lake of a yellow dye, in an amount sufficient to produce a film coloured aubergine purple on the skin, lips or nails.

The coloured inorganic pigment [A] represents from 0.1 to 10% by weight, advantageously from 0.3 to 5% by weight, of the weight of the composition.

The pigment [B] represents from 0.5 to 20% by weight, advantageously from 3 to 10% by weight, of the weight of the composition.

According to one embodiment:
 the coloured inorganic pigment [A] represents from 0.1 to 10% of the weight of the composition, and
 the pigment [B] represents from 0.5 to 20% of the weight of the composition.

According to another embodiment:
 the coloured inorganic pigment [A] represents from 0.3 to 5% by weight of the weight of the composition, and the pigment [B] represents from 3 to 10% by weight of the weight of the composition.

More particularly, the composition comprises from 0.3 to 5% by weight, advantageously from 0.3 to 1.5%, by weight, of at least one pigment [A] chosen from black iron oxides, carbon black and their mixtures.

Preferably, the pigment [B]/pigment [A] ratio by weight is greater than 1 and preferably between 2 and 15, for example between 2 and 12.

In addition, the cosmetic base of the composition of the invention can comprise cosmetically acceptable excipients and/or cosmetic active agents.

The cosmetic base can in particular comprise excipients which make it possible to obtain the desired texture (hardness, feel, and the like) and satisfactory organoleptic characteristics to make possible application to the skin or lips which is pleasant, a hold which is suited to the use, a consonant attractive rendering, in particular in terms of colour (hue and saturation) and of gloss, and a stability acceptable from the viewpoint of existing standards.

The cosmetic base thus advantageously comprises at least one fatty phase comprising a structuring agent for said fatty phase.

The fatty-phase structuring agent (which is also sometimes referred to as fatty-phase gelling agent) is advantageously chosen from polyamide polymers, L-glutamide derivatives, pyrogenic silicas, copolymers comprising at least one styrene unit which are or are not hydrogenated, or one of their mixtures.

The polyamide polymer is advantageously chosen from Ethylenediamine/Hydrogenated Dimer Dilinoleate Copolymer bis-di-$C_{14-18}$ Alkyl-Amide copolymers, such as the copolymer having the INCI name Bis-Dioctadecylamide Dimer Dilinoleic Acid/Ethylenediamine Copolymer.

The structuring agent can comprise a mixture of dibutyl lauroyl glutamide and of a hydrogenated styrene/methylstyrene/indene copolymer.

The composition according to the invention thus advantageously comprises from 10 to 50% by weight, more preferably from 15 to 30% by weight, of the composition of a structuring agent, preferably of a polyamide polymer.

The fatty phase preferably comprises a non-volatile hydrogenated polyalkylene oil, advantageously hydrogenated polyisobutene. This oil is preferably present in the composition in an amount such that the [hydrogenated polyalkylene]/[polyamide polymer] ratio by weight is within a range from 5/1 to 3/2, preferably between 4/1 and 2/1.

The fatty phase can also comprise a fatty acid ester, such as a hydroxystearate ester and in particular ethylhexyl hydroxystearate. This fatty acid ester is present in the composition in an amount such that the [fatty acid esters]/[polyamide polymer] ratio by weight is within a range from 1/4 to 4/1 and preferably between 1/3 and 3/2.

The fatty phase can also comprise a fatty alcohol, such as cetyl alcohol.

The cosmetic base in which the pigments are dispersed in order to produce the change in colour can be of the type of those conventionally used in cosmetic compositions for caring for or making up the lips, which comprise waxes. The presence of these waxy compounds renders these bases opaque, which may possibly detrimentally affect the intensity of the colour of the body of the composition but, however, does not affect the effect of change in colour as the basis of the present invention.

The base can also be translucent or substantially transparent. In this embodiment, the base comprises very little wax, preferably less than 5% by weight of wax and more preferably less than 3% by weight of wax. Said base can advantageously be devoid of wax.

Mention may be made, among the waxes, of beeswax, lanolin derivatives, carnauba, candelilla, ouricury or Japan wax, cocoa butter, paraffin, petrolatum or lignite waxes, microcrystalline waxes, ozokerites, polyethylene waxes, silicone waxes, hydrogenated castor oil, hydrogenated jojoba oil, hydrogenated palm oil, hydrogenated tallow, hydrogenated coconut oil and their mixtures.

According to a particularly preferred use, the composition comprises:
   from 0.1 to 10% by weight, advantageously from 0.3 to 5% by weight, of pigment [A], advantageously of a black iron oxide,
   from 0.5 to 20%, advantageously from 3 to 10% by weight, of pigment [B], advantageously chosen from lakes of a red dye, lakes of a blue dye, lakes of a yellow dye or a mixture of at least two of these lakes,
   from 10 to 30% by weight of at least one fatty-phase structuring polymer chosen from polyamide polymers, advantageously Bis-Dioctadecylamide Dimer Dilinoleic Acid/Ethylenediamine copolymer,
   from 30 to 80% by weight of a hydrogenated polyalkylene, advantageously hydrogenated polyisobutene,
   from 1 to 20% by weight of a fatty acid ester comprising at least one free hydroxyl group, advantageously ethylhexyl hydroxystearate.

In this particularly preferred alternative form of the invention, the pigment [A] comprises a black iron oxide or carbon black and represents from 0.3 to 2% by weight of the composition, preferably from 0.4 to 1.5% by weight of the composition.

In this particularly preferred alternative form of the invention, the composition can additionally comprise:
   from 0.5 to 5% by weight of at least one fatty alcohol comprising from 8 to 30 carbon atoms, advantageously cetyl alcohol,
   from 0.5 to 5 are by weight of structuring agent derived from glutamides, advantageously a dibutyl lauroyl glutamide mixture, and/or
   from 1 to 15% by weight of a copolymer comprising styrene, advantageously a hydrogenated styrene/methylstyrene/indene copolymer.

The composition can additionally comprise at least one cosmetic active agent chosen from moisturizing agents or humectants, antiageing agents, antimicrobial agents, screening agents which protect from UV radiation, and their mixtures. The composition can additionally comprise one or more excipients chosen from preservatives, antioxidants, fragrances, surface-active agents, rheology agents and their mixtures.

According to a particularly preferred use, the composition according to the invention is substantially anhydrous, in the sense that it comprises less than 5% by weight of water, preferably less than 2% by weight of water and more preferably less than 1% by weight of water.

The present invention is particularly suitable for the preparation of a cosmetic composition intended for making up the lips but also relates to any cosmetic composition for making up the nails or the skin, in particular the skin of the face or body.

The composition film according to the invention, applied to the lips or the skin, starting from the composition of the invention, additionally exhibits excellent hold over time.

The invention also relates to a range of make-up products each comprising a composition as described above. The range of products is understood to mean generally a group of several compositions in accordance with the description which has just been made thereof, optionally packaged in a packaging, for example a group of compositions which are simultaneously provided on a sales site and which differ essentially in the nature of the pigments present in them.

According to one embodiment, the invention relates to a group of several compositions which comprise the same transparent base and different pigments [A] and/or [B].

Said products exhibit an identical or substantially identical colour in their body, so that it is not possible or very difficult to distinguish them from one another, and deposit films, after they have been applied to the skin, lips or superficial body growths, having different colours.

The invention also relates to a kit of cosmetic compositions for making up the skin, lips or superficial body growths, comprising at least two compositions as defined above, in which kit said compositions differ in their second colour.

In this kit, the first colour of the compositions is preferably black.

The composition as described above can be obtained according to a process according to which:
 the base of the composition is prepared, in particular by mixing and heating the excipients,
 the pigments are dispersed in an oil, in order to prepare a pigment paste,
 the base and the pigment paste are mixed and then the mixture is poured into a mould or into a packaging.

The composition of the invention exhibits a texture suitable for use as make-up composition. It is possible to withdraw a sufficient amount thereof with a finger or a suitable device and to apply it subsequently. It is also possible to form it by moulding. The composition of the invention can have a solid, pasty or liquid texture.

The composition can, for example, be packaged in pots or else jars, from which the composition is withdrawn.

According to a preferred use, the composition thus prepared is moulded in the form of sticks. The forming is advantageously carried out by pouring casts into moulds, advantageously made of metal or silicone, which casts are subsequently attached to mechanisms constituting a component of the final packaging.

Another subject matter of the invention is targeted at a cosmetic make-up method, characterized in that it comprises the application of a cosmetic composition as defined above or prepared according to the process described above on the skin of a portion of the face and/or of the body and/or the lips, in particular in order to obtain an effect of making up the lips and/or a portion of the face and/or the body.

In this method, the composition advantageously exhibits a first colour in its body and the application of said composition on the skin, lips or superficial body growths reveals a second colour distinct from the first.

The composition according to the invention can be applied as a film directly on the lips or can be applied as surface or top coat over a colourless lipstick base itself advantageously transparent or translucent.

A "lipstick base" is defined as a colourless composition applied directly on the lips prior to the application of a coloured lipstick film.

The lipstick base applied as a film on the lips can make it possible to prolong the attractive effect of the make-up by improving the hold of the lipstick film, for example by preventing or slowing down the migration of the compounds of the film of the coloured composition used, or else can contribute emollience, moisturizing and/or gloss.

Other purposes, characteristics and advantages of the invention will become clearly apparent to a person skilled in the art as a result of reading the examples, which are given solely by way of illustration and thus should not in any way limit the scope of the invention. The examples form an integral part of the present invention and thus have a general scope.

Furthermore, in the examples below, all the percentages are given by weight, unless otherwise indicated, and the temperature is expressed in degrees Celsius, unless otherwise indicated, and the pressure is atmospheric pressure, unless otherwise indicated.

Example 1

The composition below can be used as lipstick. The percentages are expressed by weight of the final composition.

| Phase A | |
|---|---|
| Polyethylene wax MW = 500 | 5.1 |
| Microcrystalline wax | 2.6 |
| Candelilla wax | 5.7 |
| Phase B | |
| Acrylates/stearyl acrylate/dimethicone methacrylate copolymer | 11.4 |
| Trimethylpentaphenyltrisiloxane | 11.4 |
| Tridecyl isononanoate | 11.8 |
| Phase C | |
| Hydrogenated polyisobutene | 12.3 |
| Octyldodecyl neopentanoate | 10.6 |
| Pentaerythrityl tetraisostearate | 7.2 |
| Polyglyceryl-2 triisostearate | 1.5 |
| Phase D | |
| Black iron oxide | 0.4 |
| Blue 1 lake | 0.2 |
| Yellow 5 lake | 0.2 |
| Red 28 lake | 4.3 |
| Hydrogenated polyisobutene | 15 |

Process for the Preparation of the Composition:

The components of phase A are melted at 95° C. with stirring (Rayneri TurboTest, 300 revolutions/mn).

Phase B and then phase C are added, and melting is allowed to take place with stirring.

The pigments of phase D are ground in the presence of hydrogenated polyisobutene. This phase is subsequently added to the prepared liquid phase.

When the body is perfectly homogeneous, it is run into cylindrical moulds with a diameter of 12.7 mm and allowed to cool.

The formula of the example comprises waxy compounds. The presence of waxes slightly opacities the body but not the hue.

The application on the lips of this composition makes possible the deposition of a film having a colour which differs from the colour of the body.

The body of the composition exhibits a black colour. The film applied exhibits an unexpected raspberry pink colour.

It is thus possible to obtain the desired effect with a base comprising a significant fraction of waxy compounds.

The difference in colour between that of the stick and that of a deposited layer of composition on blank paperboard was measured by sliding the stick over the surface of the paperboard. The colorimetric parameters of the two were measured with a CS 1000 spectroradiometer (Minolta). Each measurement was carried out on five different areas of the paperboard or of the composition.

|  | L* | a* | b* | ΔE* |
|---|---|---|---|---|
| Spreading | 48 | 44 | −22 | 53 |
| Stick | 20 | 8 | 5 |  |

Example 2

The composition below can be used as lipstick and comprises a transparent base. The percentages are expressed by weight of the final composition.

| Phase A | |
|---|---|
| Bis-dioctadecylamide dimer dilinoleic acid/ ethylenediamine copolymer | 16.5 |
| Ethylhexyl hydroxystearate | 8.5 |
| Hydrogenated polyisobutene | 47.2 |
| Phase B | |
| Cetyl alcohol | 2 |
| Hydrogenated styrene/methylstyrene/indene copolymer | 5 |
| Dibutyl lauroyl glutamide | 2 |
| Phase C | |
| Red 28 lake | 4.5 |
| Black iron oxide | 1 |
| Hydrogenated polyisobutene | 14.5 |

These phases are prepared separately and are then successively mixed under hot conditions, with stirring with a Turrax and at 95° C., in order to ensure that the combined mixture is homogeneous.

The coloured composition is applied directly on the lips or after the application of a lipstick base. In both cases, it exhibits excellent hold.

The body of the composition, in the form of a stick with a diameter of 12.7 mm, exhibits a black colour. The film applied on the lips exhibits an unexpected red colour.

The difference in colour between that of the stick and that of a deposited layer of composition was measured in accordance with the method of Example 1.

|  | L* | a* | b* | ΔE* |
|---|---|---|---|---|
| Spreading | 43 | 34 | 6 | 35 |
| Stick | 20 | 7 | 2 |  |

Example 3

The composition below can be used as lipstick. The percentages are expressed by weight of the final composition.

| Phase A | |
|---|---|
| Bis-dioctadecylamide dimer dilinoleic acid/ ethylenediamine copolymer | 16.5 |
| Ethylhexyl hydroxystearate | 12 |
| Hydrogenated polyisobutene | 40.5 |
| Phase B | |
| Cetyl alcohol | 3.2 |
| Hydrogenated styrene/methylstyrene/indene copolymer | 7 |
| Dibutyl lauroyl glutamide | 0.8 |
| Phase C | |
| Black iron oxide | 0.5 |
| Blue 1 lake | 0.7 |
| Red 28 lake | 1.5 |
| Yellow 6 lake | 2.3 |
| Hydrogenated polyisobutene | 15 |

The composition is prepared according to the same process as in Example 2. The body, in the form of a stick with a diameter of 12.7 mm, exhibits a black colour. On application, the colour of the film is chocolate brown.

The difference in colour between that of the stick and that of a deposited layer of composition was measured in accordance with the method of Example 1.

|  | L* | a* | b* | ΔE* |
|---|---|---|---|---|
| Spreading | 50 | 26 | 0 | 39 |
| Stick | 17 | 5 | 5 |  |

Example 4

The composition below can be used lipstick. The percentages are expressed by weight of the final composition.

| Phase A | |
|---|---|
| Bis-dioctadecylamide dimer dilinoleic acid/ ethylenediamine copolymer | 16.5 |
| Ethylhexyl hydroxystearate | 12 |
| Hydrogenated polyisobutene | 40.5 |
| Phase B | |
| Cetyl alcohol | 3.2 |
| Hydrogenated styrene/methylstyrene/indene copolymer | 7 |
| Dibutyl lauroyl glutamide | 0.8 |
| Phase C | |
| Black iron oxide | 0.5 |
| Titanium dioxide | 0.2 |
| Blue 1 lake | 1 |
| Red 28 lake | 1.3 |
| Yellow 6 lake | 1.3 |
| Red 7 lake | 0.7 |
| Hydrogenated polyisobutene | 15 |

The composition is prepared according to the same process as in Example 1. The stick exhibits a black colour.

On application, the colour of the film applied on the lips is aubergine purple.

The difference in colour between that of the stick and that of a deposited layer of composition was made in accordance with the method of Example 1.

|  | L* | a* | b* | ΔE* |
|---|---|---|---|---|
| Spreading | 52 | 27 | −29 | 46 |
| Stick | 26 | 3 | 1 |  |

The invention claimed is:

1. A lipstick composition for making up lips, producing a change in color upon application on the lips, comprising:
    a lipstick base;
    0.3 to 1.5% by weight of black iron oxide as one colored inorganic pigment [A]; and
    3 to 10% by weight of at least one colored organic dye lake pigment [B] selected from the group consisting of red, orange, green, yellow, blue lakes and mixtures thereof,
    wherein the ratio by weight for pigment [B]/pigment [A] in the composition is between 2 and 15,
    wherein said composition having a thickness of between 5 and 20 mm exhibits a black first color, the composition having a thickness of less than 1 mm exhibits a second color, and the ΔE* colorimetric difference between the first color and the second color is at least 30 units, said ΔE* colorimetric difference being defined by the formula $$\Delta E^* = \sqrt{(L_1-L_2)^2 + (a_1-a_2)^2 + (b_1-b_2)^2}$$

in which $L_1$, $a_1$ and $b_1$ are the coordinates in the CIE Lab colorimetric space of the first color and $L_2$, $a_2$ and $b_2$ are those of the second color and
    wherein the lipstick composition comprises less than 1% by weight in total of opacifying filler(s) selected from the group consisting of talc; starch, kaolin, zinc and titanium oxides, calcium carbonate, silica, metal soaps derived from organic carboxylic acids, synthetic polymer powders and their mixtures.

2. Composition according to claim 1, wherein the dye lakes are chosen from FD&C Blue No. 1, FD&C Green No. 3, D&C Green No. 5, D&C Orange No. 4, D&C Orange No. 5, D&C Orange No. 10, FD&C No. Red 3, D&C Red No. 6, D&C Red No. 7, D&C Red No. 9, D&C Red No. 13, D&C Red No. 19, D&C Red No. 21, D&C Red No. 22, D&C Red No. 27, D&C Red No. 28, D&C Red No. 30, D&C Red No. 33, D&C Red No. 36, FD&C Red No. 40, FD&C Yellow No. 5, FD&C Yellow No. 6, D&C Yellow No. 10 and cochineal carmine.

3. Composition according to claim 1, additionally comprising a pearlescent agent chosen from:
    mica covered with titanium oxide, bismuth oxychloride, titanium oxide-coated mica covered with iron oxide, titanium oxide-coated mica covered with ferric blue or with chromium oxide, titanium-oxide coated mica covered with an organic pigment, and pigments based on bismuth oxychloride.

4. Composition according to claim 1, wherein the base comprises at least one fatty phase and one structuring agent for said fatty phase chosen from polyamide polymers, pyrogenic silicas, copolymers comprising at least one styrene unit, and their mixtures.

5. Composition according to claim 4, wherein the fatty-phase structuring agent comprises a mixture of dibutyl lauroyl glutamide and a hydrogenated styrene/methylstyrene/indene copolymer.

6. Composition according to claim 4, wherein the fatty-phase structuring agent comprises the copolymer bis-dioctadecylamide dimer dilinoleic acid/ethylenediamine copolymer.

7. Composition according to claim 1, being in anhydrous form.

8. Cosmetic make-up method, comprising the application of a composition as defined in claim 1 on the skin, lips or superficial body growths.

9. Cosmetic make-up method according to claim 8, wherein the composition exhibits a first colour in its body and in that the application of said composition on the skin, lips or superficial body growths reveals a second colour distinct from the first.

* * * * *